United States Patent [19]

Kühn

[11] Patent Number: 5,227,602

[45] Date of Patent: Jul. 13, 1993

[54] PROCESS FOR MANUFACTURING TOOTH REPLACEMENTS BY SPARK EROSION AND DEVICE FOR CLAMPING, INSERTING AND TRUING PLASTER MODELS OR COPPER ELECTRODES FOR THE SPARK-EROSION MANUFACTURE OF TOOTH REPLACEMENTS

[75] Inventor: Walter H. Kühn, Dunningen, Fed. Rep. of Germany

[73] Assignee: Krupp Medizintechnik GmbH, Essen, Fed. Rep. of Germany

[21] Appl. No.: 849,405

[22] PCT Filed: Oct. 22, 1990

[86] PCT No.: PCT/DE90/00798

§ 371 Date: Apr. 23, 1992

§ 102(e) Date: Apr. 23, 1992

[87] PCT Pub. No.: WO88/06429

PCT Pub. Date: Sep. 7, 1988

[30] Foreign Application Priority Data

Oct. 24, 1989 [DE] Fed. Rep. of Germany ....... 3935275

[51] Int. Cl.⁵ ............... B23H 9/00; A61C 13/02; C25D 7/00
[52] U.S. Cl. ............... 219/69.17; 164/DIG. 4; 249/54; 433/167
[58] Field of Search ............... 219/69.17; 164/DIG. 4; 249/54; 433/167, 200.1, 215, 218; 205/70

[56] References Cited

U.S. PATENT DOCUMENTS

| | | | |
|---|---|---|---|
| 2,094,308 | 9/1937 | Suell | 205/70 |
| 3,997,637 | 12/1976 | Rogers | 205/70 |
| 4,363,627 | 12/1982 | Windeler | 433/167 |
| 4,451,236 | 5/1984 | Tarasov et al. | 433/218 |
| 4,627,136 | 12/1986 | Kreylos | 29/160.6 |
| 4,734,173 | 3/1988 | Walter | 204/129.1 |
| 4,904,348 | 2/1990 | Domes | 205/67 |
| 5,057,017 | 10/1991 | Sillard | 433/167 |

FOREIGN PATENT DOCUMENTS

| | | | |
|---|---|---|---|
| 3222616 | 12/1983 | Fed. Rep. of Germany | 433/167 |
| 3320902 | 3/1985 | Fed. Rep. of Germany | . |
| 225513 | 6/1987 | Fed. Rep. of Germany | 433/167 |

Primary Examiner—Geoffrey S. Evans
Attorney, Agent, or Firm—Herbert Dubno; Andrew Wilford

[57] ABSTRACT

A method of making a dental prosthesis by forming a model of a tooth stump, coating with a layer of electrically conductive material, galvanically plating over the conductive material with a layer of copper, exposing occlusal surfaces of the model, coating the exposed occlusal surfaces of the model with an electrically conductive material followed by a galvanic plating on the model occlusal surfaces, and separating the copper layers form each other at about the tooth equator into an occlusal mold/electrode and a stump mold/electrode. The electrodes are used in a spark erosion process to form a dental prosthesis from a solid matrix body.

15 Claims, 7 Drawing Sheets

PROCESS FOR MANUFACTURING TOOTH REPLACEMENTS BY SPARK EROSION AND DEVICE FOR CLAMPING, INSERTING AND TRUING PLASTER MODELS OR COPPER ELECTRODES FOR THE SPARK-EROSION MANUFACTURE OF TOOTH REPLACEMENTS

CROSS REFERENCE TO RELATED APPLICATIONS

This application is the national phase of application PCT/DE90/00798 filed Oct. 22, 1992 and claiming the priority of German application P 3,935,274 filed Oct. 24, 1989.

FIELD OF THE INVENTION

The invention relates to a method of making tooth replacement parts such as crown bridges.

The invention further relates to an apparatus for holding, setting, and aligning a plaster model or copper electrodes for the spark-erosion manufacture of tooth replacement parts, comprised of a support table settable at any desired inclination.

BACKGROUND OF THE INVENTION

*Deutschen Zahnartzlichen Zeituno*, 41, pages 525-526 (1986) describes the production of a metal sleeve crown from solid material by means of spark erosion. Here an individual wax body modeled on a casting or in the mouth of the patient is plated about 1 mm thick with copper above and below a plane defined by the crown equator. This galvanically shaped element is separated at the equator so as to produce two shaping electrodes by means of which a tooth replacement part can be produced from a metal blank. Both shaping electrodes sink corresponding to the erosion removal into the metal body and thus form the tooth replacement part, for instance a top crown. The advantage of this method is that standard noble metals and nonnoble metal alloys can be machined, in particular those which cannot or can only be cast with great difficulty. During the tooth replacement part production mistakes which are caused by errors in the dimensions or interfitting of the dies during casting are largely eliminated. The disadvantage of this method is however that the natural teeth or the correspondingly shaped wax model has no clearly defined equator plane, since the tooth equator extends both vertically or horizontally in a nonstraight manner. If one assumes a central section plane it is necessary to take undercuts into account that cannot be produced by spark erosion.

Thus U.S. Pat. No. 4,904,348 describes how to mount the positive wax models on a common carrier such that casting molds can be made and shaped. The individual tooth replacement parts are aligned in a common equatorial plane that is set at the widest part of their section such that this equatorial plane is the split plane for the subsequent eroding electrodes. In a further step of the method the spaces between the individual replacement parts up to the equatorial plane are filled in order at first to produce the upper electrode, so that during filling of the space between the individual teeth of the replacement wax model one or more orienting pins is set perpendicular to the equatorial plane. After hardening of the cast mass, for instance a silicone mixture, the surfaces are cleared of impurities and the clean model is plated with a thin layer of silver which serves as a conductive layer for the subsequent eroding electrodes After galvanic copper plating these are stabilized by reinforcement and can be used as eroding electrodes. To produce second electrodes the first model is inverted by 180° and is set in a form whose base is filled with a hardenable support mass. After hardening of the support mass another silver layer is applied to the surfaces and plated over with copper. The disadvantage of this is that an arbitrary equatorial plane as described above must be set, and in addition the individual wax models are aligned in a casting mold that is positioned by means of spacers which must be separately built. In order to spare time during the spark-erosion as desired it is not possible that in a unit of time a predetermined number of electrode sparks, according to the applied voltage, can be produced.

In general the above-described methods further have the disadvantage that the wax model is unprotected not only during pulling off of the plaster model but also during preparation or production of the copper electrode and is in danger of being deformed. The exact alignment of the wax model or of the copper electrodes relative to each other is also not described in the art.

OBJECTS OF THE INVENTION

It is therefore an object of the present invention to improve on the described method so that independent of manual dexterity of the production person it is assured that the wax model remains unharmed during the various treatment steps and further that means are provided which ensure an exact alignment of the plaster model as well as of the copper electrodes relative to each other. Furthermore it is an object of this invention to provide an apparatus designed for carrying out this alignment.

SUMMARY OF THE INVENTION

In the above described method the object is obtained in that on a degreased sealed stump of a positive plaster model a thin-walled, slippery, stable, and relatively inelastic synthetic-resin cap is mounted which stops on the occlusal side shortly before the preparation border and over which is subsequently formed the wax model by shaping a preparation border and simultaneous establishment of the tooth equator, before a silicone layer extending to the tooth equator is mounted occlusally on it, while meanwhile the plaster model is set as a master model with the inset wax parts in an adjustment device, that in addition on the silicone layer a hardenable plastic is layered on which a horizontally extending and overreaching orientation plate is set so that this orientation plate is fixed after hardening of the plastic with the plastic, that this orientation plate together with the affixed plastic, the silicone layer, the wax model, and the plastic cap is lifted from the plaster stump and a filler is applied from the apical side from the tooth equator to the last applied plastic as well as to the adjacent surfaces of the orientation plate and the apical sides of the (first) plaster cup, the exposed wax-model surfaces and adjacent areas right up to the orientation plate are coated with an electrically conductive material and thereover for galvanic purposes with a copper layer. Then the copper layer together with the wax model are separated and from the occlusal side right up to the tooth equator first a conductive material and then for galvanic purposes a copper layer is applied. On both sides of the copper layer on the external surfaces of each a pin or other suitable connecting element is mounted, with the pins being arranged axially and radially in line with each other.

The above described degreasing and sealing of the stomp as well as the mounting of the thin-wall plastic cap serves to protect the wax model from the inside so that in particular during separation of the wax model from the plaster model no deformation of the wax model can occur.

The tooth equator of the model wax model is exactly determined and its actual position is followed on application of this silicone layer. In order to avoid that the wax model must be pulled by hand from the master plaster model, a hardenable plastic is applied to the silicone layer on which a horizontally projecting overreaching orientation plate is set so that this orientation plate after hardening of the plastic is bonded to the plastic. Thus, if the orientation plate with the bonded layers is to be lifted from the plaster stump, this can be done with application of some force to the orientation plate while avoiding that these forces or pressures are effective on the wax model. Filling of the last-applied plastic layers serves to smooth and above all things to fill the undercuts which after a galvanic copper plating would prevent a pulling apart of the two copper electrodes. In addition the plastic is chosen with regard to the subsequently applied silver or graphite layer. The copper plating which later is used as the spark-erosion electrode creates an exact negative contour of the plaster stump as well as of the apical part of the wax model.

After this copper layer is separated together with the wax model from the silicone layer, a silver or graphite layer is applied to the exposed occlusal side down to the tooth equator so that a copper layer can be produced galvanically. During this the lower apical copper electrode can be galvanized together with the occlusal copper electrode. In order to hold the copper electrodes in a spark-erosion machine they must be provided on their back sides with fixing means, either plates, pins, or guide sleeves. To this end it is important that the fixing means be aligned both in the axial (horizontal and vertical direction) as also in the radial direction. This means that when the copper electrodes are set in each other the longitudinal axes of the pins or fixing elements must lie on a line and it must also be ensured that on subsequent spark-erosion removal the second electrode is not turned in a radial direction relative to the first. It is thus advisable to employ as fixing means such parts which are not rotation symmetrical, thus for example pins that are semicircular in section or non-round plates.

Thus the material for the plastic cap has shown to be ideally a cold acrylate-based polymer. The plastic cap should stop about 1/10 mm above of the preparation border, in order to produce in the region of the preparation border a clean wax model.

The orientation plate is formed for cost purposes of a metal and has two holes so that this plate is adjustable.

In order to protect the wax model on a separation from the plaster stump (master model) as can happen by canting or twisting by removal by hand, the orientation cap is magnetically held on a horizontal outrigger arm of an adjustment device both during setting and also during separation from the master model. Thus an exact vertical guiding in the movement direction is ensured.

If the spark-erosion removal takes place first on a roughing electrode and the fine treatment with a finished electrode, the following production of the roughing electrode is advisable. To start with as described above a 2 to 3/10 mm-thick copper layer is applied galvanically to the apical and occlusal areas. This layer is passivated on its surfaces in a bath whereupon a new layer of conductive material is plated on and the galvanic treatment is completed. The 2 to 3/10 mm-thick copper layer can subsequently be dissolved, whereupon a negative contour in the copper electrode ideal for the roughing is produced.

As described above preferably silver or graphite is used as a conductive material in the thinnest possible layer of 1 to 5 $\mu$m.

In order to save material and to reduce erosion time the spark-erosion electrodes are made as small as possible. On the other side it is indispensable that the copper halves of the electrodes extend into a region where the two halves meet at a planar surface, in practice a common annular contact surface. Preferably the entire annular common surface is connected via individual elements with the actual copper electrodes having the negative contours of the wax model which can take place by the application of corresponding silver or graphite layers.

In order to align the fixing means for the spark-erosion machine and to secure them on the galvanically produced copper electrodes these copper electrodes are set in a correspondingly shaped recess of a table with a horizontal support surface, are axially and radially aligned before a radially aligned pin fitted in an outrigger arm and carrying on its end a fixed plate is set down on the copper electrode surface, and subsequently the plate is set down on the surface and soldered or glued thereto. An axially alignment of the pin or the plate secured on its end can be done by a correspondingly arranged holding device of an outrigger arm above the table. The axial alignment of the copper electrode takes place by means of the recess, a radial alignment of the copper electrode is possible by use of an asymmetric contour and a correspondingly shaped recess. Alternative thereto it is also possible for the connecting means such as a pin, plate, sleeve or the like to be formed galvanoplastically together with the copper plating for the spark-erosion electrode as a single piece in a single working step s that a subsequent procedure such as the gluing or soldering is unnecessary.

In order always to maintain the same reference line the recess in the plate is formed of an annular planar surface and a recess in a size which is sufficient to accept the copper electrode.

Since on a spark-erosion out of stability ground only about 0.5 to 0.7 mm copper of the electrode is used, preferably the galvanic plating of the copper electrode is only carried out until the copper electrode has a thickness of about 1 mm.

For holding, setting, and aligning the plaster models or copper electrodes for the spark-erosion production of tooth parts the apparatus according to claim 15 is used. This is comprised of a holding table orientable in any desired inclination and above which is a horizontal outrigger arm mounted on a vertical column which can move up and down as well as along the column axis or over a portion of it. This column and the support table each have at least one hole for receiving a centering pin, whereby the outrigger arm is adjustable in the vertical-/axial direction relative to the support table. In addition the outrigger arm has on its underside a permanent magnet or magnetically excitable support surface for an apertured orientation plate of metal.

In order to clamp a plaster model a support table has on its upper surface holding jaws and/or a recess with at least one planar annular surface for receiving a galvanically produced copper electrode.

Preferably the region surrounding the annular surface are hollowed out like a downwardly opened recess so that it is possible to set the electrode halves straight from the bath in place and thereafter to solder or glue on the first upper electrode a fixing means according to the desired alignment and subsequently to turn the copper electrode pair through 180 and to mount a similar attachment on the second electrode. As fixing means plates can for example be used which preferably are fixed on the end of a pin so that this pin can be received in a clamping or holding device or in an internally threaded bore of the outrigger arm.

Preferably the support table has separable and exchangeable upper parts of which one is provided for holding a master model and the other is provided with a recess for holding a galvanically produced copper electrode.

BRIEF DESCRIPTION OF THE DRAWING

Embodiments by means of which the invention is further described are shown in the drawing. There is shown in.

SPECIFIC DESCRIPTION

The method according to the invention unites three different technologies which can each be carried out without particular expertise. The technologies are:
1. Dental working and production of a wax model,
2. The production of a galvanic model, and
3. The spark-erosion removal from a blank.

Disadvantages such as the production of pores, cavities, or shape changes are excluded by carrying out the below-described method.

In the production of tooth replacement parts one starts with an impression spoon from which according to the state of the art in a known matter a positive plaster model is produced. On this plaster model the plaster stumps are produced, either for crowns or for bridges, each with a correspondingly established preparation border.

The plaster stump 10 is cleaned and sealed. After drying of the sealing a plastic cap 11 of a cold acrylate-based polymer is applied which ends about 1/10 mm above the preparation border 12. This plastic cap has a thickness of from 0.5 to about 1 mm. The produced acrylic cap 11 has the advantage that by subsequent working steps no deformation of the wax model 13 can take place. Simultaneously a duplication of the desired electrode, for producing of roughing or finished electrodes, is achieved.

Modeling with wax is the basis for producing electrodes. The crown or bridge model must be so modeled that the preparation border 12 and the tooth equator 14 are optimally set. The plaster stump with the modelled wax crown 13 is subsequently set in the master model and screwed into a modelling table. All important points are now, as in standard in the art, checked with a parallelometer. Then there is applied over the wax model 13 a thin silicone layer 15 above the tooth equator which is intended to prevent the wax crown 13 from being deformed in subsequent operations and to prevent it from sticking. Subsequently the model table is set under an adjustment machine so that the axis and the size of the blank for fitting in a spark-erosion machine can be determined. A hardenable plastic 16 is applied on top of the silicone layer 15 and before hardening of this plastic 16 an orientation plate 17 of metal is set on it so that this metal plate 17 is fixedly bonded with the plastic 16 after it hardens. Subsequently the orientation plate together with the bonded layers 16, 15, 13 and 11 is lifted from the plaster stump and is filled from the apical side down to the tooth equator and over the last-applied plastic 16 as well as over the adjacent surfaces of the orientation plate 17. This filler mass is shown at 18.

Figure 2A:
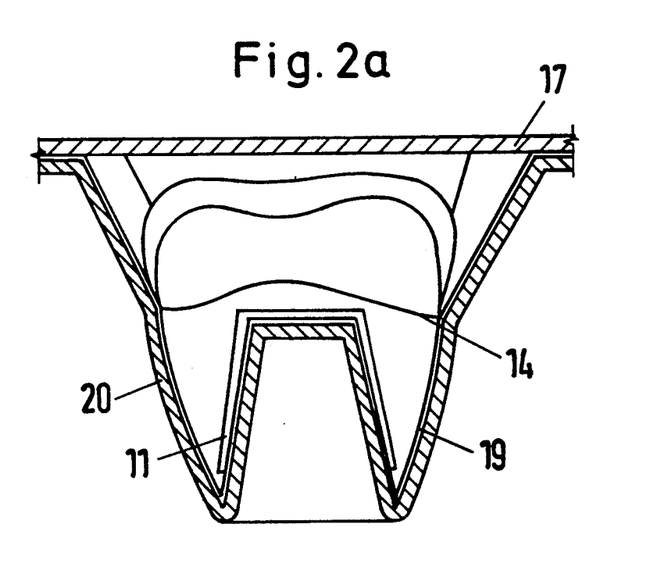
FIGS. 2a and 2b are each a cross section through a wax model with a galvanically produced copper shaped electrode on the apical side.
Figure 3A:
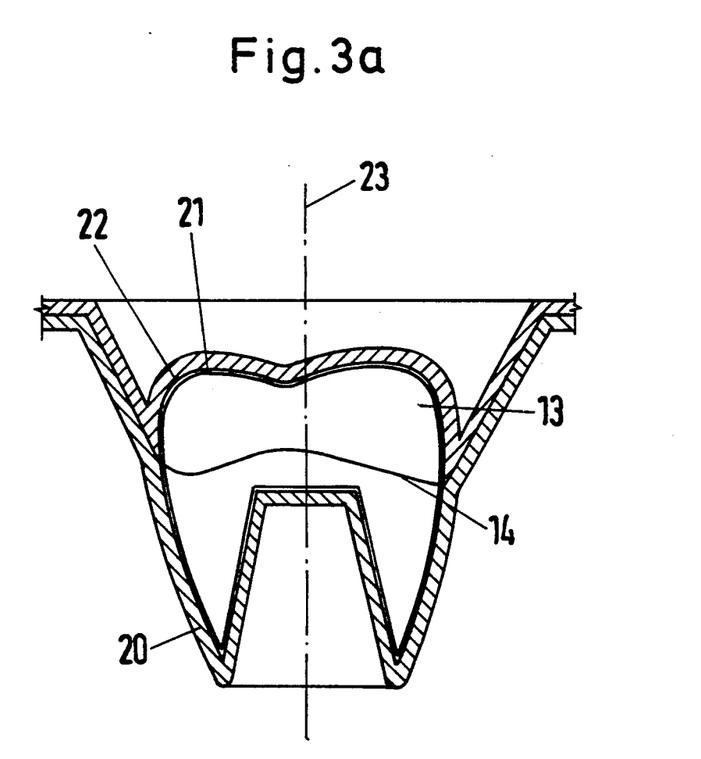
FIGS. 3a and 3b are each a section through set-together copper shaping electrodes with the wax model between them.

As seen in FIG. 2a subsequently from the apical side the underside of the orientation plate 17, the filler mask 18, the exposed wax surface 13 below the equator 14, as well as the inside of the cap 11 are coated with a silver layer 19 which serves as a basis for the copper coating 20. To this end the orientation plate is set if necessary together with further orientation plates of other models in a bedding mass or is otherwise secured to a support and put in a galvanic bath. The galvanic copper plating should have a thickness of about 1 mm. Subsequently the orientation plate together with the layers 16, 15 and 18 is separated so that one gets the produced copper layer 21 containing the wax model 13 which is exposed from the occlusal side. To this wax model 13 and the adjacent edge surfaces of the produced copper layer a silver or graphite layer 21 is applied which is the base for a copper layer 22 which is also produced in a galvanic bath. Thus all the structure shown in FIG. 3a is in a galvanic bath. After coating with a sufficiently thick copper layer 20 or 21 the bodies are taken out of the galvanic bath and the wax model is removed since it is no longer needed. The inner surfaces of the copper layers 21 and 22 correspond to the negative shape of the wax model 13. In order to be able to use the copper parts 20 and 21 as a spark-erosion electrode it is now necessary to mount on the outside fixing means. This fixing means can be formed of brazed-on pins or a plate or the like. It is only important that the fixing means be so mounted that it is axially as well as radially aligned, that is that the used fixing means must have the same orientation with respect to the axis 23 shown in FIG. 3a.

Figure 1A:
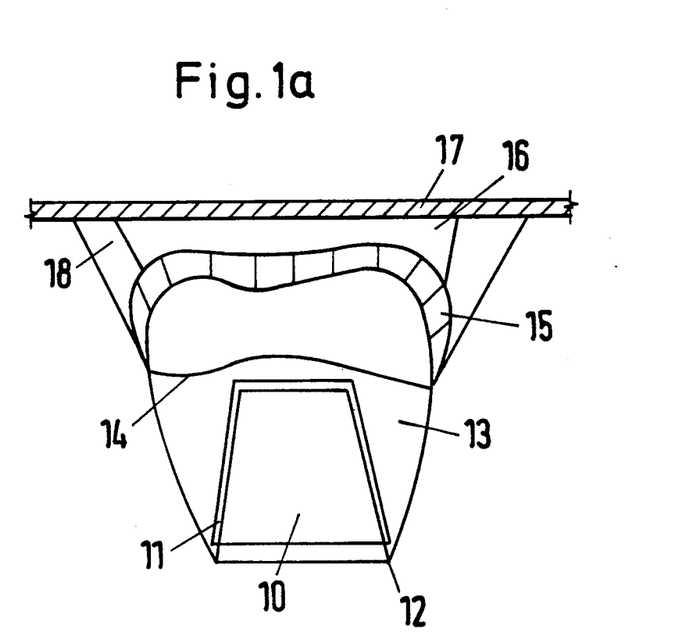
FIGS. 1a and 1b are each a cross section through a plaster stump with a formed wax model, on which various layers have been applied in schematic representation.
Figure 1B:
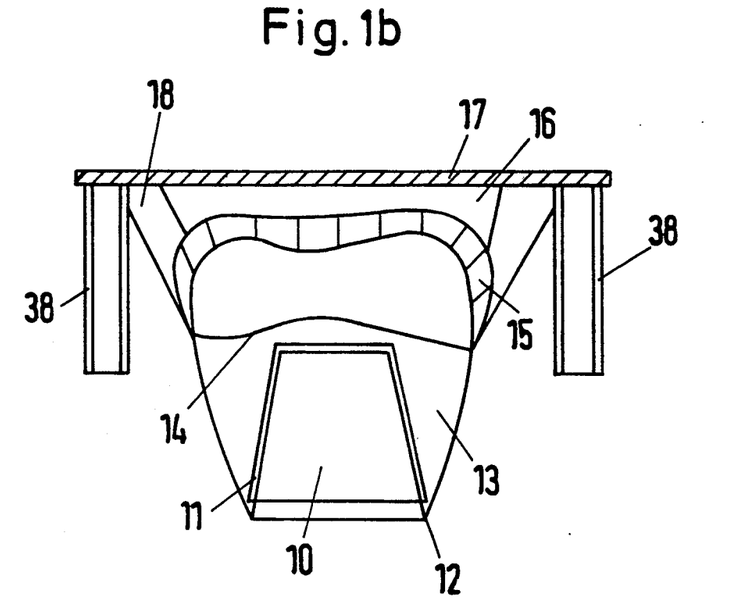
Figure 2B:
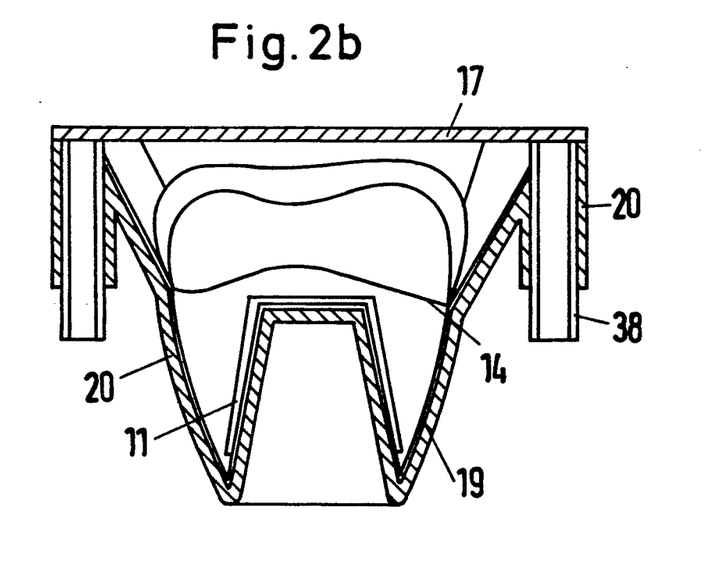
Figure 3B:
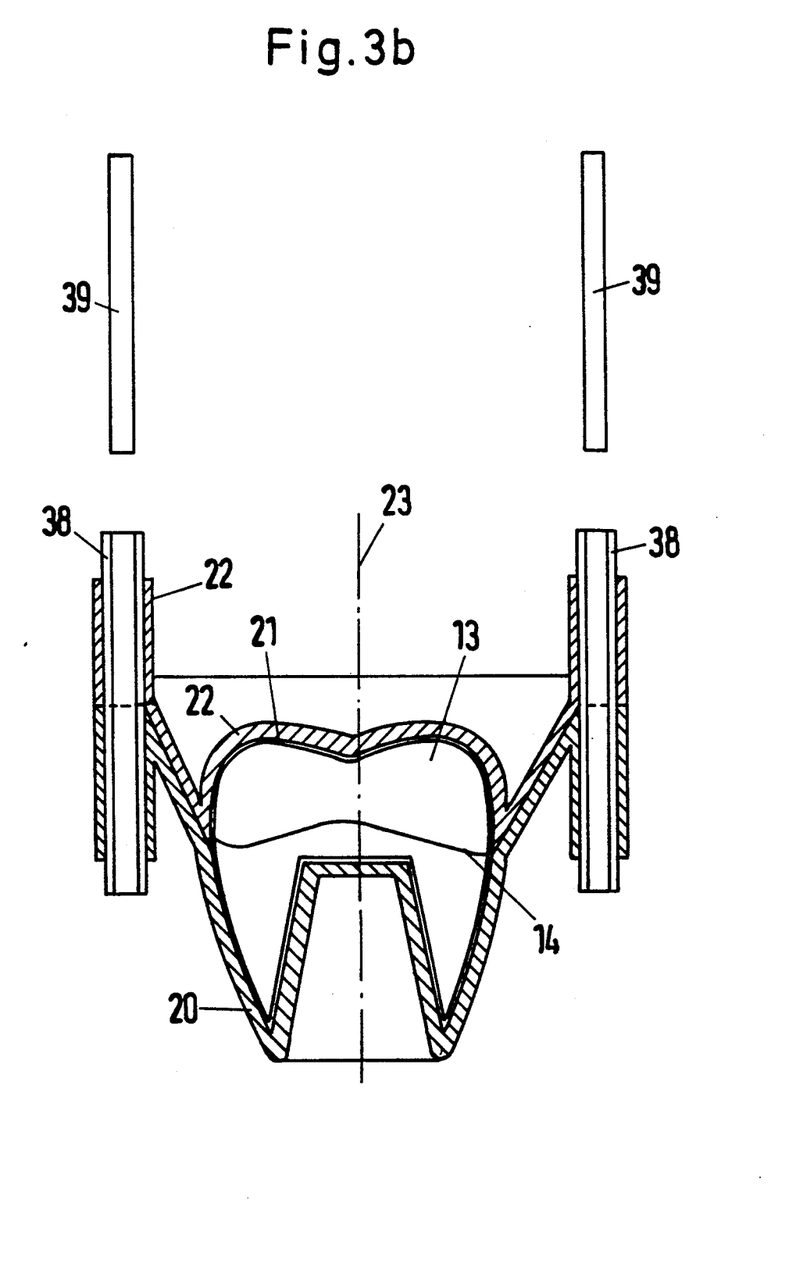

The sections shown in FIGS. 1b, 2b and 3b are different from those described above in that the connecting elements are also formed galvanoplastically, in fact as one piece together with the copper coating serving later as the spark-erosion electrode.

Figure 5:
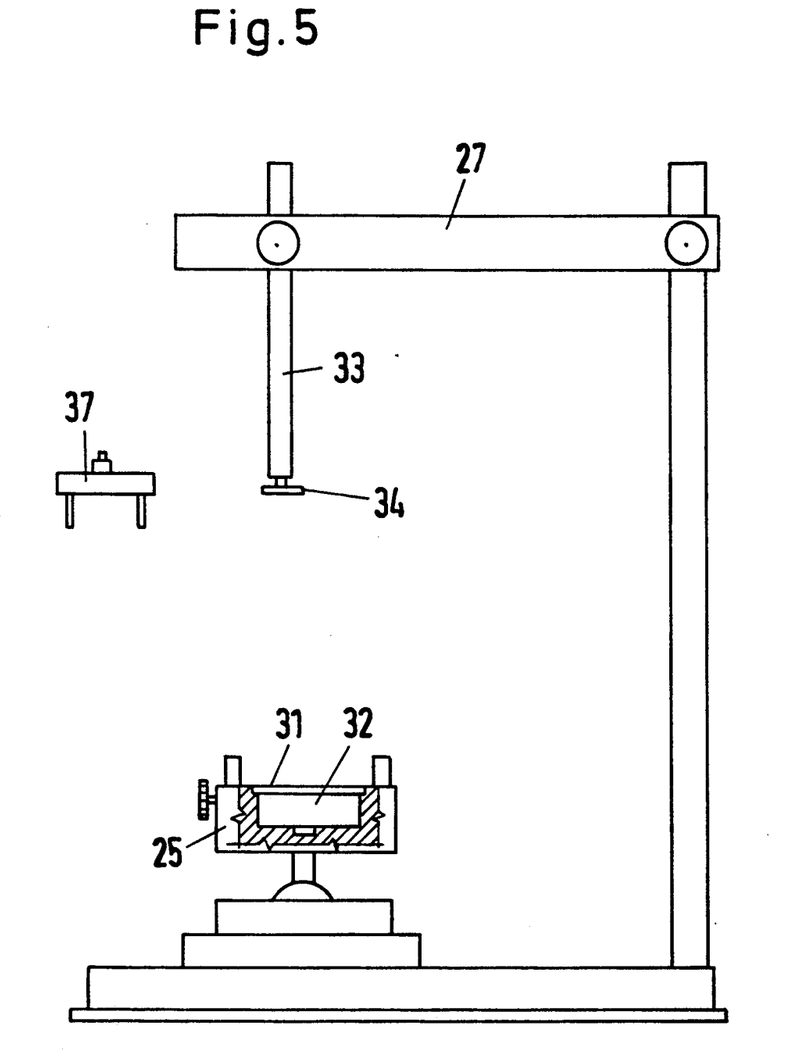
Figure 6:
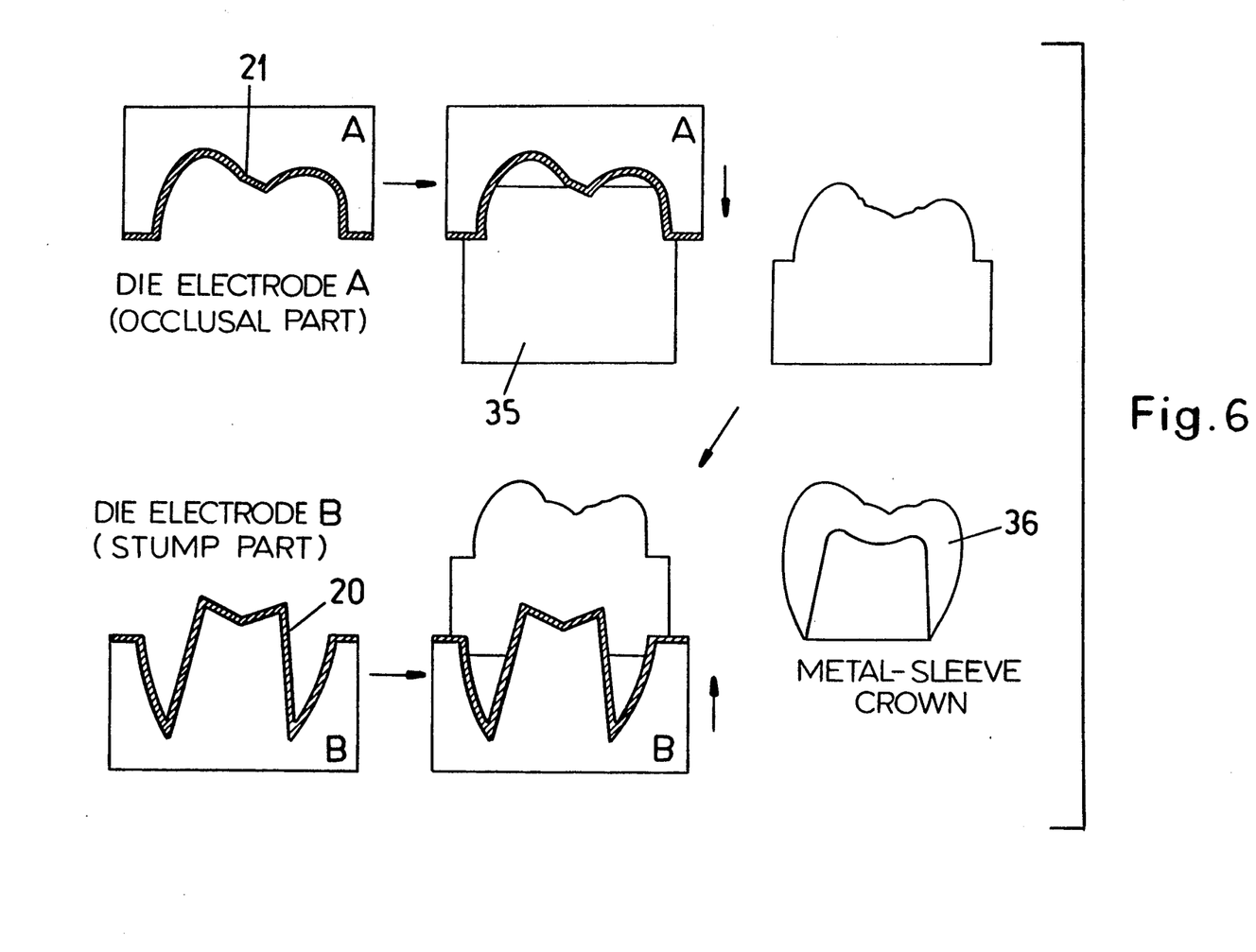
FIG. 6 is a representation of the spark-erosion method for producing a crown.

As seen in FIG. 1b by use of the apparatus 37 as shown in FIG. 5 guide sleeves or pins, for instance brass tubes 38, are formed on the wax model 13 or the layers 15, 16 and/or 18 applied thereto.

As seen in FIG. 2b the silver layer 19 is applied up to and somewhat overlapping the brass tubes 38 so that subsequently a continuous copper coating 20 can be applied. After lifting the orientation plate 17 and before galvanizing the occlusal side at first pins 39 are slipped through the brass tubes 38 for alignment and the silver layer is applied on the occlusal side right up to the region of the tube 38 whereupon subsequently the copper layer 22 is galvanically applied. In order to mount in a spark-erosion apparatus preferably the ends of the tubes over a length of about 5 mm are left free which is effected in that these ends are covered before being copper plated.

The production techniques shown in FIGS. 1a and 1b allow the connection elements to be produced galvanoplastically in a single step with the copper coating so that the gluing or soldering of the copper electrodes become unnecessary.

Figure 4:
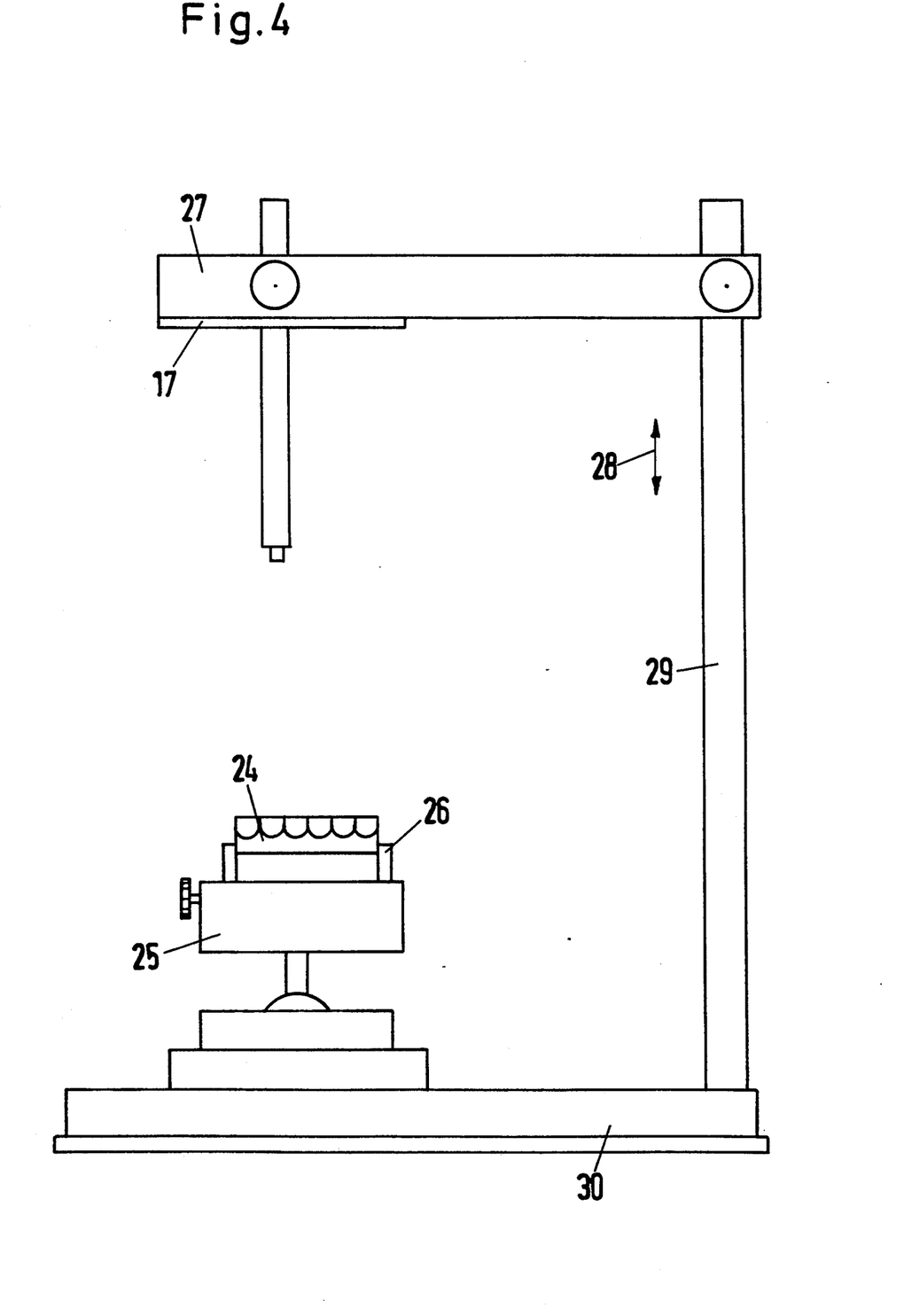
FIGS. 4 and 5 are schematic representations of the apparatus according to the invention.

An apparatus for holding a master model 24 and aligning it is shown in FIG. 4. This apparatus comprises basically a support table 25 which is pivotal in the desired spatial directions and which for example has clamping jaws 26 for holding the plaster model 24.

Above the table is an outrigger arm 27 which is movable up and down in the direction of double-headed arrow 28. This outrigger arm has like the table 25 a not shown vertical bore by means of which the outrigger arm and the table can be axially aligned relative to each other by means of a centering pin. In addition the under side of the outrigger arm 28 is magnetic and thus ideal to hold an orientation plate 17. The outrigger arm is either fixed on a vertical column 20 pivotal about its vertical axis or is itself pivotal about this vertical axis 29. The support table 25 can either be fixed with a support surface 30 or can lie on it.

The apparatus shown in FIG. 5 is mainly set up so that the support table 25 has an annular recess 31 surrounding a pocket 32. In this recess 31, 32 the body shown in FIG. 3 can be set for alignment and mounting of a connecting element. When a pin with a plate on it serves as a connecting element this pin 33 is held in a special clamp or holding device of the outrigger arm 27. By lifting of the outrigger arm 27 at first the end plate 34 comes to rest on the inset copper part and can be brazed to it or connected by means of a conductive plastic. By turning the copper double part through 180° the other side can also be mounted on a connecting apparatus. This therefore ensures that both connecting elements are aligned with respect to the axis 23 (see FIG. 3) and also radially relative to it, and it is particularly advisable that the pin 33 have a non rotation-symmetrical section. In order to produce a crown of metal a blank 35 is started with against which the copper electrode 21 is moved till the negative contour is formed by material removal. Subsequently from the other side the other electrode is moved in and the blank 35 is worked until the finished element 36 is produced. Spark-erosion removal is known in principle and is for example described in German 3,544,123, to which reference should be made.

I claim:

1. A method of making a dental prosthesis such as crowns or bridges, the method comprising the steps of:
    a) forming a positive plaster model of a tooth stump;
    b) fitting to the stump of the plaster model a thin-walled plastic cap extending from an occlusal end of the stump to immediately short of a preparation border of the stump;
    c) modelling a wax tooth-part model on the stump over the cap;
    d) applying over the wax model a silicone layer extending to a tooth equator;
    e) applying over the silicon layer a hardenable plastic;
    f) fitting a horizontally extending and overreaching orientation plate to the hardenable plastic and hardening the plastic to fix the plate therein;
    g) separating from the plaster stump the assembly comprised of the orientation plate together with the affixed plastic, the silicone layer, the wax model, and the plastic cap and thereby exposing apical surfaces of the wax model beneath the tooth equator;
    h) applying a filler between the plate and the tooth equator;
    i) coating the assembly right up to the orientation plate with an electrically conductive material;
    j) galvanically plating over the electrically conductive material a layer of copper;
    k) separating from the coated assembly the separation plate, filler, hardened plastic, and silicone and thereby exposing occlusal surfaces of the wax model;
    l) coating the exposed occlusal surfaces of the wax model with an electrically conductive material;
    m) galvanically plating over the electrically conductive material on the model occlusal surfaces a layer of copper;
    n) separating the copper layers from each other generally at the tooth equator into an occlusal mold/electrode and a stump mold/electrode and stripping the wax model from the electrodes; and
    o) employing the electrodes in a spark-erosion process to form the dental prosthesis from a solid matrix body.

2. The method defined in claim 1 wherein the plastic cap is made of a cold acrylate-based polymer.

3. The method defined in claim 1 wherein in step b) the plastic cap stops about 1/10 mm above the preparation border.

4. The method defined in one of claim 1 wherein the orientation plate is formed with two bores.

5. The method defined in claim 4 wherein the orientation plate is held by means of a magnet on a horizontal outrigger arm of an adjustment mechanism during step f).

6. The method defined in one of claims 1 wherein the copper layer of steps j) and m) is applied in a first layer between 0.2 mm and 0.3 mm thick copper layer, this first layer is passivated on its surface, a second layer of conductive material is applied to the first layer, and a second layer of the copper is applied over the second layer of conductive material.

7. The method defined in one of claim 1 wherein the conductive material is silver or graphite in a thickness of 1 $\mu$m to 6 $\mu$m.

8. The method defined in one of claims 1 wherein the layer of conductive material and the galvanic copper layer is only applied to surfaces of the wax model and the regions of its coatings and thereafter is applied to several elements leading to a ring and to partial surfaces of the ring.

9. The method defined in claim 1, further comprising the steps of
    fixing respective occlusal and stump connecting elements on the occlusal and stump electrodes; and
    interfitting the connecting elements to align the electrodes during step o).

10. The method defined in claim 9 wherein one of the connecting element is a pin and the other connecting element is a socket complementary to the pin.

11. The method defined in claim 9 wherein the connecting-element pin is fixed to the respective electrode by sequentially generally during step f)

securing same in a corresponding shaped recess of a table with a horizontal support surface,     axially and radially aligning the electrode, engaging a radially aligned pin fitted in an outrigger arm and carrying on its end a fixed plate down to the respective electrode surface, and     fixing the plate to the electrode surface.

12. The method defined in claim 9 wherein the connecting elements are fixed to the respective elements by before step j)

forming supports on the wax model, axially and radially aligning the supports, and galvanically plating copper on the supports to form the connecting elements.

13. The method defined in claim 12 wherein the supports for the subsequently galvanically produced connecting element are sleeves whose ends are covered over a length of about 5 mm before the application of the copper.

14. The method defined in claim 9 wherein during the fixing step the stump electrode is held in a recess serving as holder of an annular flat surface.

15. The method defined in claim 1 wherein the galvanic plating is carried out such that the copper electrodes have a minimal thickness of 1 mm.

* * * * *